(12) United States Patent
Keefe

(10) Patent No.: US 8,548,573 B2
(45) Date of Patent: Oct. 1, 2013

(54) DYNAMICALLY FILTERED BEAT DETECTION IN AN IMPLANTABLE CARDIAC DEVICE

(75) Inventor: James M. Keefe, Penn Valley, PA (US)

(73) Assignee: Cameron Health, Inc., San Clemente, CA (US)

( * ) Notice: Subject to any disclaimer, the term of this patent is extended or adjusted under 35 U.S.C. 154(b) by 827 days.

(21) Appl. No.: 12/689,217

(22) Filed: Jan. 18, 2010

(65) Prior Publication Data

US 2011/0178564 A1 Jul. 21, 2011

(51) Int. Cl.
*A61B 5/0452* (2006.01)

(52) U.S. Cl.
USPC .............................................. 600/509; 607/62

(58) Field of Classification Search
USPC .......................................................... 607/62
See application file for complete search history.

(56) References Cited

U.S. PATENT DOCUMENTS

| | | |
|---|---|---|
| 4,184,493 A | 1/1980 | Langer et al. |
| 4,300,567 A | 11/1981 | Kolenik et al. |
| 4,407,288 A | 10/1983 | Langer et al. |
| 4,450,527 A | 5/1984 | Sramek |
| 4,457,315 A | 7/1984 | Bennish |
| 4,595,009 A | 6/1986 | Leinders |
| 4,679,144 A | 7/1987 | Cox et al. |
| 4,693,253 A | 9/1987 | Adams |
| 4,750,494 A | 6/1988 | King |
| 4,779,617 A | 10/1988 | Whigham |
| 4,979,110 A | 12/1990 | Albrecht et al. |
| 4,989,602 A | 2/1991 | Sholder et al. |
| 5,000,189 A | 3/1991 | Throne et al. |
| 5,105,810 A | 4/1992 | Collins et al. |
| 5,184,616 A | 2/1993 | Weiss |
| 5,193,535 A | 3/1993 | Bardy et al. |
| 5,215,098 A | 6/1993 | Steinhaus et al. |
| 5,217,021 A | 6/1993 | Steinhaus et al. |
| 5,271,411 A | 12/1993 | Ripley et al. |
| 5,280,792 A | 1/1994 | Leong et al. |
| 5,299,119 A | 3/1994 | Kraf et al. |
| 5,313,953 A | 5/1994 | Yomtov et al. |
| 5,331,966 A | 7/1994 | Bennett et al. |
| 5,342,402 A | 8/1994 | Olson et al. |
| 5,342,407 A | 8/1994 | Dahl et al. |
| 5,351,696 A | 10/1994 | Riff et al. |
| 5,376,104 A | 12/1994 | Sakai et al. |

(Continued)

FOREIGN PATENT DOCUMENTS

EP 0554208 A2 8/1993

OTHER PUBLICATIONS

U.S. Appl. No. 61/255,253, filed Oct. 27, 2009, Allavatam, et al.
U.S. Appl. No. 61/255,249, filed Oct. 27, 2009, Warren, et al.

(Continued)

*Primary Examiner* — Joseph Dietrich
(74) *Attorney, Agent, or Firm* — Schwegman Lundberg & Woessner, P.A.

(57) ABSTRACT

Methods and implantable devices that detect cardiac events using dynamic filtering. Illustratively, default filtering is performed except for a predefined period of time following detection of cardiac events, during which post-beat filtering is performed instead. The example post-beat filtering applies a narrower pass-band to the signal than the default filtering in order to attenuate T-waves more greatly than the default filtering during a time period after a detected event that is expected to correspond to occurrence of T-waves.

20 Claims, 5 Drawing Sheets

(56) References Cited

U.S. PATENT DOCUMENTS

| | | |
|---|---|---|
| 5,423,326 A | 6/1995 | Wang et al. |
| 5,447,519 A | 9/1995 | Peterson |
| 5,522,852 A | 6/1996 | White et al. |
| 5,534,019 A | 7/1996 | Paspa |
| 5,545,186 A | 8/1996 | Olson et al. |
| 5,558,098 A | 9/1996 | Fain |
| 5,607,455 A | 3/1997 | Armstrong |
| 5,658,317 A | 8/1997 | Haefner et al. |
| 5,709,215 A | 1/1998 | Perttu et al. |
| 5,817,134 A | 10/1998 | Greenhut et al. |
| 5,827,197 A | 10/1998 | Bocek et al. |
| 5,857,977 A | 1/1999 | Caswell et al. |
| 5,991,657 A | 11/1999 | Kim |
| 6,041,251 A | 3/2000 | Kim et al. |
| 6,047,210 A | 4/2000 | Kim et al. |
| 6,052,617 A | 4/2000 | Kim |
| 6,058,328 A | 5/2000 | Levine et al. |
| 6,095,987 A | 8/2000 | Shmulewitz et al. |
| 6,115,628 A | 9/2000 | Stadler et al. |
| 6,144,879 A | 11/2000 | Gray |
| 6,148,230 A | 11/2000 | KenKnight |
| 6,223,078 B1 | 4/2001 | Marcovecchio |
| 6,230,055 B1 | 5/2001 | Sun et al. |
| 6,236,882 B1 | 5/2001 | Lee et al. |
| 6,240,313 B1 | 5/2001 | Esler |
| 6,266,554 B1 | 7/2001 | Hsu et al. |
| 6,280,462 B1 | 8/2001 | Hauser et al. |
| 6,308,095 B1 | 10/2001 | Hsu et al. |
| 6,334,071 B1 | 12/2001 | Lu |
| 6,377,844 B1 | 4/2002 | Graen |
| 6,381,493 B1 | 4/2002 | Stadler et al. |
| 6,393,316 B1 | 5/2002 | Gillberg et al. |
| 6,397,100 B2 | 5/2002 | Stadler et al. |
| 6,411,844 B1 | 6/2002 | Kroll et al. |
| 6,438,410 B2 | 8/2002 | Hsu et al. |
| 6,449,503 B1 | 9/2002 | Hsu |
| 6,493,579 B1 | 12/2002 | Gilkerson et al. |
| 6,493,584 B1 | 12/2002 | Lu |
| 6,505,068 B2 | 1/2003 | Bonnet et al. |
| 6,516,225 B1 | 2/2003 | Florio |
| 6,561,984 B1 | 5/2003 | Turcott |
| 6,567,691 B1 | 5/2003 | Stadler |
| 6,574,505 B1 | 6/2003 | Warren |
| 6,575,912 B1 | 6/2003 | Turcott |
| 6,587,720 B2 | 7/2003 | Hsu et al. |
| 6,625,490 B1 | 9/2003 | McClure et al. |
| 6,643,549 B1 | 11/2003 | Bradley et al. |
| 6,647,292 B1 | 11/2003 | Bardy et al. |
| 6,684,100 B1 | 1/2004 | Sweeney et al. |
| 6,699,200 B2 | 3/2004 | Cao et al. |
| 6,708,058 B2 | 3/2004 | Kim et al. |
| 6,708,062 B2 | 3/2004 | Ericksen et al. |
| 6,721,597 B1 | 4/2004 | Bardy et al. |
| 6,728,572 B2 | 4/2004 | Hsu et al. |
| 6,731,978 B2 | 5/2004 | Olson et al. |
| 6,745,068 B2 | 6/2004 | Koyrakh et al. |
| 6,754,528 B2 | 6/2004 | Bardy et al. |
| 6,889,079 B2 | 5/2005 | Bocek et al. |
| 6,909,916 B2 | 6/2005 | Spinelli et al. |
| 6,950,702 B2 | 9/2005 | Sweeney |
| 7,016,730 B2 | 3/2006 | Ternes |
| 7,020,523 B1 | 3/2006 | Lu et al. |
| 7,027,856 B2 | 4/2006 | Zhou et al. |
| 7,027,858 B2 | 4/2006 | Cao et al. |
| 7,027,862 B2 | 4/2006 | Dahl et al. |
| 7,031,764 B2 | 4/2006 | Schwartz et al. |
| 7,062,314 B2 | 6/2006 | Zhu et al. |
| 7,062,315 B2 | 6/2006 | Koyrakh et al. |
| 7,062,322 B2 | 6/2006 | Stadler et al. |
| 7,076,289 B2 | 7/2006 | Sarkar et al. |
| 7,085,599 B2 | 8/2006 | Kim et al. |
| 7,117,035 B2 | 10/2006 | Wagner et al. |
| 7,149,575 B2 | 12/2006 | Ostroff et al. |
| 7,162,301 B2 | 1/2007 | Kim et al. |
| 7,167,747 B2 | 1/2007 | Gunderson et al. |
| 7,184,815 B2 | 2/2007 | Kim et al. |
| 7,184,818 B2 | 2/2007 | Kim et al. |
| 7,191,004 B2 | 3/2007 | Kim et al. |
| 7,194,302 B2 | 3/2007 | Bardy et al. |
| 7,218,966 B2 | 5/2007 | Haefner |
| 7,236,819 B2 | 6/2007 | Brockway et al. |
| 7,248,921 B2 | 7/2007 | Palreddy et al. |
| 7,266,409 B2 | 9/2007 | Gunderson |
| 7,283,863 B2 | 10/2007 | Gunderson |
| 7,302,294 B2 | 11/2007 | Kamath et al. |
| 7,330,757 B2 | 2/2008 | Ostroff et al. |
| 7,346,392 B2 | 3/2008 | KenKnight |
| 7,376,458 B2 | 5/2008 | Palreddy et al. |
| 7,379,772 B2 | 5/2008 | Bardy et al. |
| 7,386,342 B1 | 6/2008 | Falkenberg et al. |
| 7,392,085 B2 | 6/2008 | Warren et al. |
| 7,444,182 B2 | 10/2008 | Ostroff et al. |
| 7,447,540 B1 | 11/2008 | Nabutovsky et al. |
| 7,467,009 B2 | 12/2008 | Palreddy et al. |
| 7,477,935 B2 | 1/2009 | Palreddy et al. |
| 7,496,408 B2 | 2/2009 | Ghanem et al. |
| 7,496,409 B2 | 2/2009 | Greenhut et al. |
| 7,499,750 B2 | 3/2009 | Haefner et al. |
| 7,522,959 B2 | 4/2009 | Hauser et al. |
| 7,546,159 B1 | 6/2009 | Nabutovsky et al. |
| 7,555,335 B2 | 6/2009 | Kamath et al. |
| 7,559,900 B2 | 7/2009 | Gillberg |
| 7,567,835 B2 | 7/2009 | Gunderson et al. |
| 7,570,997 B2 | 8/2009 | Lovett et al. |
| 7,593,771 B2 | 9/2009 | Yonce et al. |
| 7,623,909 B2 | 11/2009 | Sanghera et al. |
| 7,623,913 B2 | 11/2009 | Phillips |
| 7,623,916 B2 | 11/2009 | Julian |
| 7,655,014 B2 | 2/2010 | Ko et al. |
| 7,682,316 B2 | 3/2010 | Anderson et al. |
| 7,684,864 B2 | 3/2010 | Olson et al. |
| 7,715,906 B2 | 5/2010 | Krause et al. |
| 7,734,345 B2 | 6/2010 | Cinbis |
| 7,761,142 B2 | 7/2010 | Ghanem et al. |
| 7,774,049 B2 | 8/2010 | Ghanem et al. |
| 7,783,354 B2 | 8/2010 | Gunderson |
| 7,797,036 B2 | 9/2010 | Zhang et al. |
| 7,865,233 B2 | 1/2011 | Haefner |
| 7,894,894 B2 | 2/2011 | Stadler et al. |
| 7,904,142 B2 | 3/2011 | Kim et al. |
| 7,904,153 B2 | 3/2011 | Greenhut et al. |
| 7,907,993 B2 | 3/2011 | Ghanem et al. |
| 7,983,749 B2 | 7/2011 | Warren |
| 2004/0215239 A1 | 10/2004 | Favet et al. |
| 2004/0215240 A1 | 10/2004 | Lovett et al. |
| 2004/0220628 A1 | 11/2004 | Wagner |
| 2004/0230229 A1 | 11/2004 | Lovett et al. |
| 2005/0107838 A1 | 5/2005 | Lovett et al. |
| 2005/0131464 A1 | 6/2005 | Heinrich et al. |
| 2005/0154421 A1 | 7/2005 | Ousdigian |
| 2006/0122676 A1 | 6/2006 | Ko et al. |
| 2006/0167502 A1 | 7/2006 | Haefner |
| 2006/0167503 A1 | 7/2006 | Warren et al. |
| 2006/0167504 A1 | 7/2006 | Warren et al. |
| 2006/0241701 A1 | 10/2006 | Markowitz et al. |
| 2007/0032829 A1 | 2/2007 | Ostroff |
| 2007/0049975 A1 | 3/2007 | Cates et al. |
| 2007/0135847 A1 | 6/2007 | Kenknight |
| 2007/0142736 A1 | 6/2007 | Cazares et al. |
| 2007/0156190 A1 | 7/2007 | Cinbis et al. |
| 2007/0179539 A1 | 8/2007 | Degroot et al. |
| 2007/0179540 A1 | 8/2007 | Stegemann et al. |
| 2007/0232944 A1 | 10/2007 | Ghanem et al. |
| 2007/0232945 A1 | 10/2007 | Kleckner et al. |
| 2007/0232948 A1 | 10/2007 | Stadler et al. |
| 2007/0233198 A1 | 10/2007 | Ghanem et al. |
| 2007/0260151 A1* | 11/2007 | Clifford .................. 600/509 |
| 2007/0276445 A1 | 11/2007 | Sanghera et al. |
| 2008/0015647 A1 | 1/2008 | Palreddy et al. |
| 2008/0077030 A1 | 3/2008 | Ostroff et al. |
| 2008/0086174 A1 | 4/2008 | Libbus et al. |
| 2008/0091242 A1 | 4/2008 | Kamath et al. |
| 2008/0132965 A1 | 6/2008 | Ostroff et al. |
| 2008/0161870 A1 | 7/2008 | Gunderson |

| | | |
|---|---|---|
| 2008/0172098 A1 | 7/2008 | Gunderson |
| 2008/0183085 A1 | 7/2008 | Van Oort et al. |
| 2008/0188901 A1 | 8/2008 | Sanghera et al. |
| 2008/0215110 A1 | 9/2008 | Gunderson |
| 2008/0221632 A1 | 9/2008 | Bardy et al. |
| 2008/0228093 A1 | 9/2008 | Dong et al. |
| 2008/0243200 A1 | 10/2008 | Scinicariello et al. |
| 2008/0262559 A1 | 10/2008 | Zhang et al. |
| 2008/0275516 A1 | 11/2008 | Ghanem et al. |
| 2008/0275517 A1 | 11/2008 | Ghanem et al. |
| 2008/0275519 A1 | 11/2008 | Ghanem et al. |
| 2008/0275521 A1 | 11/2008 | Warren et al. |
| 2009/0036788 A1 | 2/2009 | Nabutovsky et al. |
| 2009/0036944 A1 | 2/2009 | Fonte |
| 2009/0043352 A1 | 2/2009 | Brooke et al. |
| 2009/0054796 A1 | 2/2009 | Sanghera et al. |
| 2009/0054938 A1 | 2/2009 | Ostroff et al. |
| 2009/0093731 A1 | 4/2009 | Palreddy et al. |
| 2009/0156957 A1 | 6/2009 | Linder et al. |
| 2009/0157128 A1 | 6/2009 | Seim et al. |
| 2009/0157132 A1 | 6/2009 | Linder et al. |
| 2009/0157137 A1 | 6/2009 | Gilkerson et al. |
| 2009/0187227 A1 | 7/2009 | Palreddy et al. |
| 2009/0198296 A1 | 8/2009 | Sanghera et al. |
| 2009/0228057 A1 | 9/2009 | Allavatam et al. |
| 2009/0240157 A1 | 9/2009 | Liam et al. |
| 2009/0240300 A1 | 9/2009 | Liam et al. |
| 2009/0259271 A1 | 10/2009 | Allavatam et al. |
| 2010/0004713 A1 | 1/2010 | Warren et al. |
| 2010/0094369 A1 | 4/2010 | Allavatam et al. |
| 2010/0152798 A1 | 6/2010 | Sanghera et al. |
| 2010/0152799 A1 | 6/2010 | Sanghera et al. |
| 2010/0331904 A1 | 12/2010 | Allavatam et al. |
| 2011/0098585 A1 | 4/2011 | Warren et al. |
| 2011/0098775 A1 | 4/2011 | Allavatam et al. |

OTHER PUBLICATIONS

U.S. Appl. No. 61/221,316, filed Jun. 29, 2009, Allavatam, et al.

Gunderson et al., "An Algorithm to Predict Implantable Cardioverter-Defibrillator Lead Failure," JACC, Nov. 2004, vol. 44, No. 9, pp. 1898-1902.

Olson et al., "Onset and Stability for Ventricular Tachyarrhythmia Detection in an Implantable Pacer-Cardioverter-Defibrillator," IEEE, (1987) pp. 167-170.

Schuder, "The Role of an Engineering Oriented Medical Research Group in Developing Improved Methods and Devices for Achieving Ventricular Defibrillation: The University of Missouri Experience," PACE, vol. 16, Jan. 1993, pp. 95-124.

Schwake et al., "Komplikationen nit Sonden bei 340 Patienten mit einem Implantierbaren Kardioverter/Defibrillator," Z Kardiol (1999)vol. 88, No. 8 pp. 559-565.

Swerdlow, et al., "Advanced ICD Troubleshooting: Part I," online article at http://www.medscape.com/viewarticle/520588_print, accessed and printed Jul. 7, 2009, indicates publication Jan. 9, 2006 (publication date not confirmed).

Throne, "A Comparison of Four New Time-Domain Techniques for Discriminating Monomorphic Ventricular Tachycardia from Sinus Rhythm Using Ventricular Waveform Morphology," IEEE Transactions on Biomedical Engineering, vol. 38, No. 6, Jun. 1991, pp. 561-570.

* cited by examiner

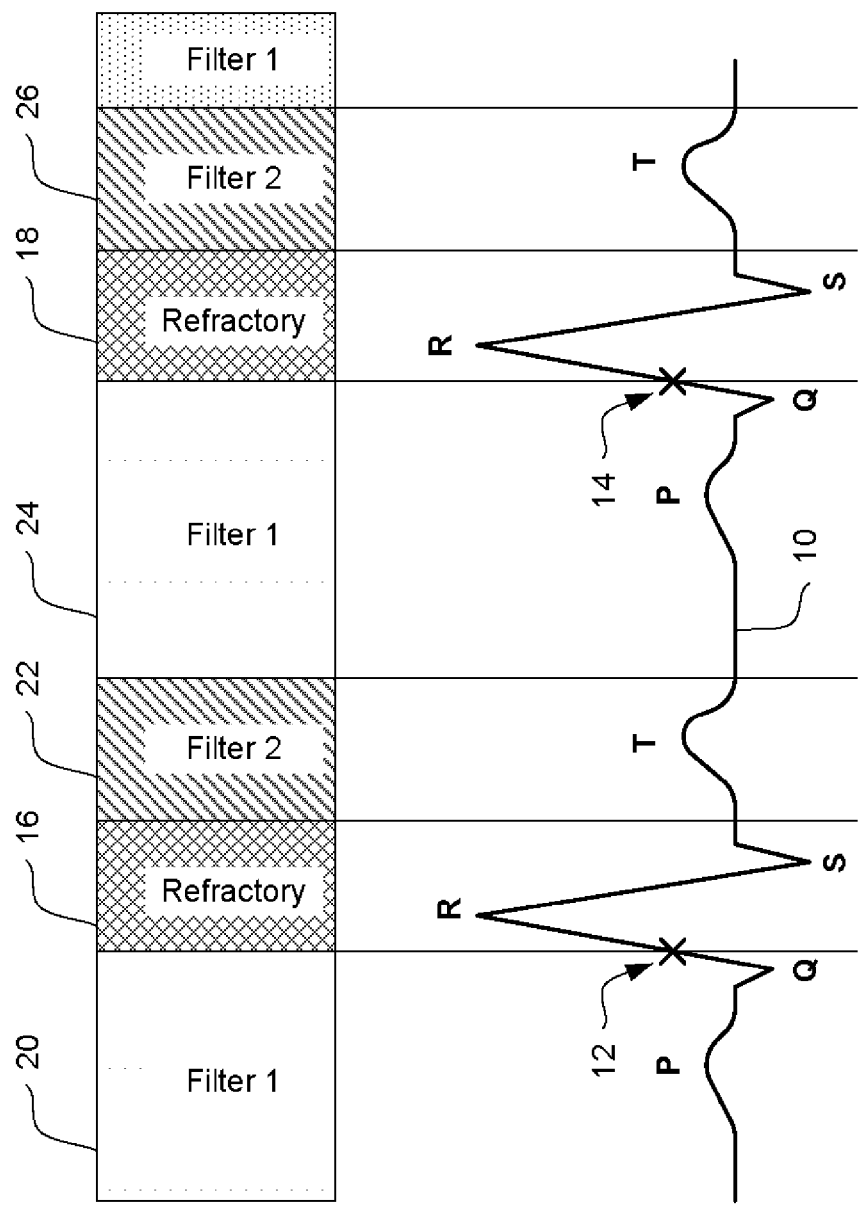

DYNAMICALLY FILTERED BEAT DETECTION IN AN IMPLANTABLE CARDIAC DEVICE

FIELD

The present invention relates to the field of implantable cardiac devices, including monitoring and stimulus devices. More particularly, the present invention relates to beat detection in such devices.

SUMMARY

The present invention, in a first illustrative embodiment, includes a method of detecting cardiac events in which a first filtering approach is used as a default and, when a beat is detected, a second filtering approach is used during an interval following the detected beat. In some examples, a refractory period is defined around the detected beat, and the second filtering approach is used during an interval following the refractory period. The second filtering approach may include more aggressive and frequency specific filtering directed at eliminating certain cardiac artifacts such as T-waves, relative to the first filtering approach. In addition to methods, the present invention also includes embodiments in the form of systems and implantable devices.

BRIEF DESCRIPTION OF THE DRAWINGS

FIG. 2 illustrates the application of filtering and refractory periods to a cardiac signal for an illustrative embodiment;

DETAILED DESCRIPTION

The following detailed description should be read with reference to the drawings. The drawings, which are not necessarily to scale, depict illustrative embodiments and are not intended to limit the scope of the invention. Any references to other patents or patent applications are intended as illustrative of useful methods or devices and are not intended to foreclose suitable alternatives.

Figure 1:
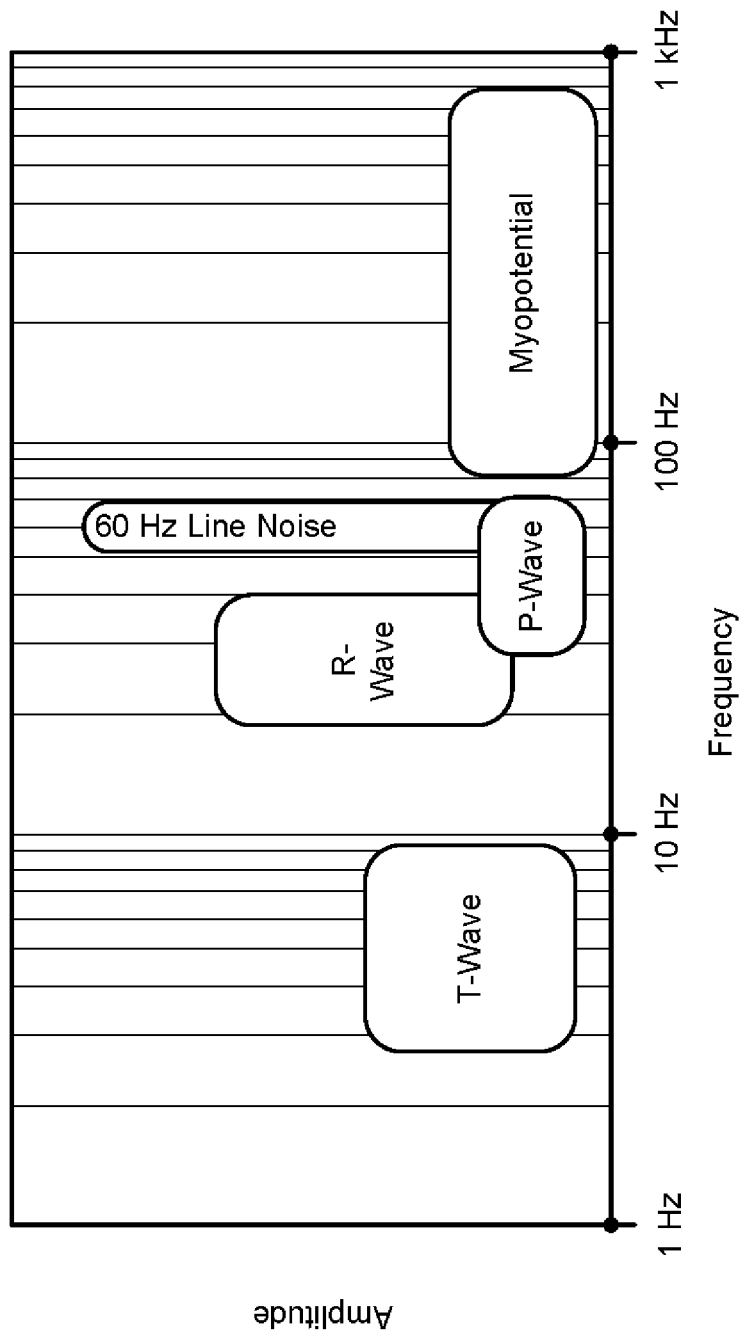
FIG. 1 illustrates the frequency content of typical signals that an implantable cardiac device encounters during operation.

FIG. 1 illustrates the frequency content of typical signals that an implantable cardiac device encounters during operation. The signals shown omit the potential impact of motion artifact, but cover many other potential system inputs. The height of each block generally corresponds to typical amplitude ranges. The horizontal axis represents frequency in log format.

Cardiac signal is characterized in the chart of FIG. 1 by T-waves, R-waves and P-waves; other "waves" in the cardiac signal are typically of lesser amplitude and are not represented in the drawing. The QRS complex is often referred to as the heart "beat". Non-cardiac sources of interference can include myopotentials, which are generated by any non-cardiac muscle in the body, external line noise and/or other sources of noise. The external line noise varies in frequency depending on geographic region. In the example shown, external line noise is shown as 60 Hz line noise, which would occur in the United States. As is known in the art, other geographies may have 50 Hz line noise instead. Other sources of interference, whether intermittent or pervasive, are omitted for simplicity.

As can be seen, T-wave and R-wave signals are relatively lower in frequency than the line noise and myopotentials, and T-waves typically have a lower frequency content than the R-waves. Thus, frequency selectivity can be used to eliminate certain non-cardiac signals. It has been known to use notch filtering to attenuate line noise, and bandpass filtering can also be used. For example, U.S. Pat. No. 6,754,528 suggests the use of a Narrow Band filter with corner frequencies at approximately 10 Hz and 30 Hz, with a parallel Wide Band filter having corner frequencies at approximately 1 Hz and 50 Hz. In U.S. Pat. No. 6,754,528, the outputs of the two filters may be used for different purposes, for example, with the Narrow Band filtered signal used for event detection and the Wide Band filtered signal used for beat morphology analysis. In additional examples, filters may be modified in response to detected conditions, such as in US Patent Application Publication Number 2007-0032829, wherein a high pass filter can be bypassed in response to high beat rate to avoid attenuating low frequency components of the signal.

Several illustrative embodiments perform a different process in which cardiac signal data is filtered according to its timing relative to detected events. In other illustrative embodiments, beat detection is performed using differently filtered signals at different times relative to previous detected events. FIG. 2 provides a graphic illustration.

FIG. 2 illustrates the application of filtering and refractory periods to a cardiac signal for an illustrative embodiment. A refractory period is a time period during which additional cardiac events are not declared by the system; sensing input circuitry may be on or off during refractory, as desired. In some examples, signals are captured during the refractory period to support morphology analysis of detected events.

The captured cardiac signal trace is shown at 10 and includes repetitive signal features marked according to standard convention as P, Q, R, S and T waves. Detection of events for this signal can be performed using a detection profile, for example as set forth in commonly assigned US Patent Application Publication Number 2009-0228057, titled ACCURATE CARDIAC EVENT DETECTION IN AN IMPLANTABLE CARDIAC STIMULUS DEVICE, the disclosure of which is incorporated herein by reference. For example, the captured signal is compared to a detection threshold and when the amplitude of the captured signal exceeds the detection threshold, a detected event is declared. For simplicity of illustration, detection profiles are not shown in FIG. 2. Any other suitable methods of detection may be used instead.

Detections are indicated at the X-es shown at 12 and 14. Upon each detection 12, 14, corresponding refractory periods 16, 18 start. Each refractory period 16, 18 has a predetermined duration. As noted in the 2009-0228057 Publication, the refractory periods may vary in duration in response to detected conditions such as amplitude similarities and/or calculated event/beat rate.

Ordinarily the system uses a default filter noted as "Filter 1," as indicated at 20, 24. Filter 1 may use frequency selective filtering such as bandpass filtering and/or notch filtering, as desired and known in the art. Upon termination of the refractory periods 16, 18, a time period is defined for use of "Filter 2", as indicated at 22, 26. In the illustrative example, Filter 2 provides different frequency selectivity to the detection circuitry/module of the system when compared to Filter 1, which is applied during other time periods shown at 20, 24. Filter 1 may be considered the default filter for the system, while Filter 2 is applied for a period of time following refractory. As can be seen from comparison to the signal 10, the time periods during which Filter 2 is applied at 22, 26 correspond to T-waves occurring in the cardiac signal 10. The use of Filter 1 and Filter 2 may parallel other steps in the overall detection method, such as the use of constant threshold periods as shown in the 2009-0228057 Publication. In another example, a third filter, Filter 3, is applied during the refractory period or another predetermined period initially following the detection, where Filter 3 is designed to support morphology analysis of the system, as in U.S. Pat. No. 6,754,528.

In several examples, Filter 2 is designed to more greatly attenuate frequencies that correspond to T-waves. For example, Filter 2 may include additional attenuation for frequencies between 3-15 Hz. In one example, Filter 1 sets the high-pass frequency corner of its passband in the range of 1-5 Hz, while Filter 2 moves the high-pass frequency corner of its passband to a higher level in the range of 3-10 Hz. Following are some illustrative numeric examples:

| Filter 1 High Pass | Filter 2 High Pass | Filters 1 and 2 Low Pass |
|---|---|---|
| 1 Hz | 3 Hz | 40 Hz |
| 1 Hz | 10 Hz | 40 Hz |
| 3 Hz | 10 Hz | 50 Hz |
| 5 Hz | 12 Hz | 40 Hz |

As noted, the Filter 2 approach can be applied for a limited period of time following refractory. In one example, the refractory period is in the range of 100-250 milliseconds, and the time period for applying Filter 2 is in the range of 100-200 milliseconds. For example, the refractory period may be about 160 milliseconds and the time period for Filter 2 may be about 140 milliseconds. In another example, the refractory period may be variable depending on cardiac conditions such as rate, and the time period for Filter 2 may adjust such that the sum of the refractory plus Filter 2 timer periods is generally constant in the range of 250-450 milliseconds. The examples may help to attenuate the T-wave during a time period where the system is susceptible to R-wave double/triple detection and T-wave overdetection.

Figure 3A:
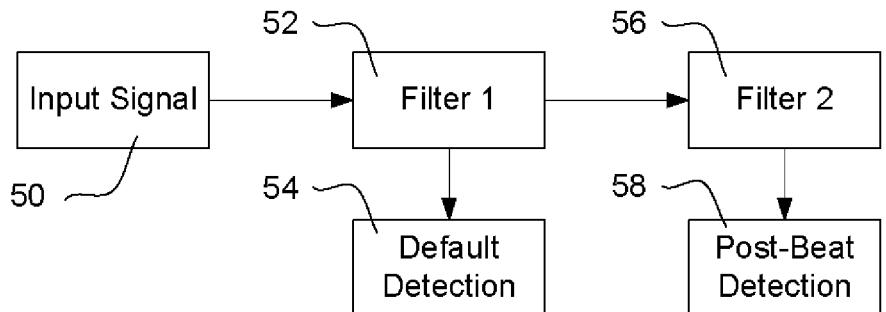
FIGS. 3A-3C demonstrate three configurations for performing filtering and detection in illustrative embodiments.
Figure 3B:
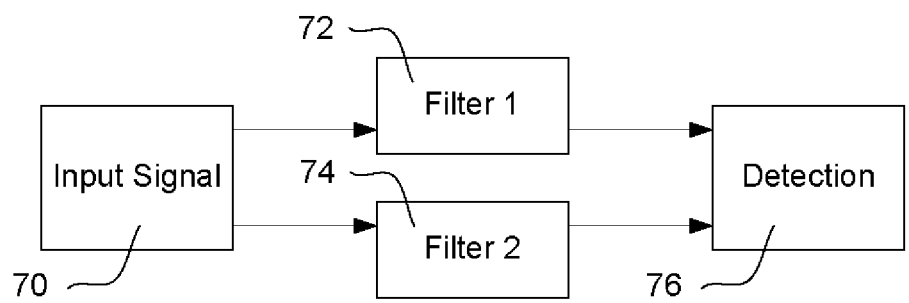
Figure 3C:
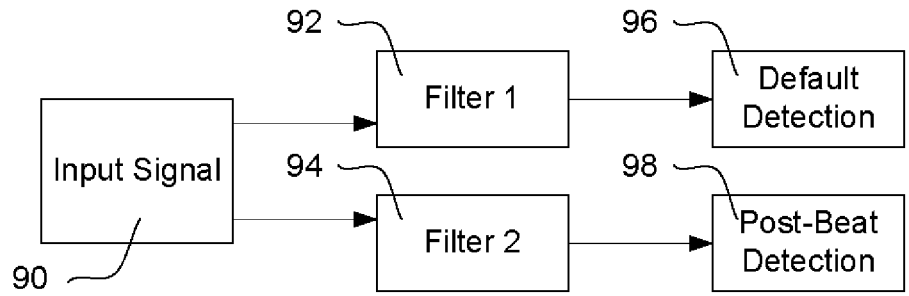

FIGS. 3A-3C demonstrate three configurations for performing filtering and detection in illustrative embodiments. Each example references an input signal 50, 70, 90. The input signals 50, 70, 90 may be analog pre-amplifier, analog post-amplifier, and/or digital signals.

FIG. 3A shows an example in which the input signal 50 is fed to a cascade of filters, including Filter 1, at 52, which provides an input to a default detection block 54, and Filter 2, at 56, which provides an input to a Post-Beat detection block 58. FIG. 3B shows an example in which the input signal 70 is fed to Filter 1, at 72, in parallel with Filter 2, at 74, and detection block 76 selects which filter 72, 74 to use at any given time depending upon when the last beat was detected. FIG. 3C shows an example in which the input signal 90 is fed to Filter 1, at 92, and Filter 2, at 94, in parallel, and each of the filters 92, 94 is used by different detection blocks, the default detection block 96 or the post-beat detection block 98.

Reviewing FIGS. 3A-3C, it should be noted that depending upon the design of analog and/or digital filters in these systems, it can be difficult to turn on or turn off filters without introducing additional filter-related-artifacts to the signal. Thus, FIGS. 3A and 3C both show examples in which separate detection systems are applied to different filter outputs. In FIG. 3B it is assumed that filter switching can occur without creating additional noise. In addition, each example of FIGS. 3A-3C shows multiple filters and, if desired, one of the filters may be applied in the digital domain while the other is applied in the analog domain. In some examples, the system may simply switch additional filtering components in/out of the circuit during operation, without adding additional layers of detection circuits. While separate blocks are shown for the different filters, it should be understood that physically separate implementation is not necessary; separate data processing may occur within a single physical unit such as a microcontroller. The use of separate blocks is merely for illustrative purposes.

Figure 4:
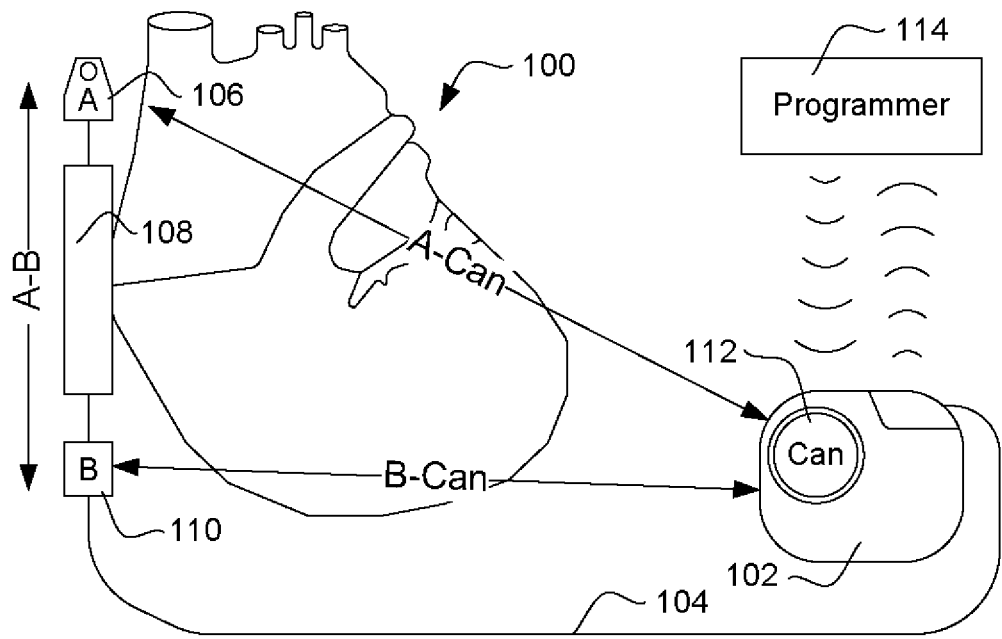
FIG. 4 shows an illustrative subcutaneous implantable defibrillator.

FIG. 4 shows an illustrative subcutaneous implantable defibrillator. The illustrative system is shown relative to a patient's heart 100 and includes a canister 102 coupled to a lead 104 having electrodes 106, 108, 110. The canister 102 includes an electrode 112, such that the implanted system provides multiple sensing vectors shown at A-Can (between electrodes 106 and 112), B-Can (between electrodes 110 and 112) and A-B (between electrodes 106 and 110). Additional sensing vectors may use electrode 108, which is shown as a relatively larger electrode and may take the form of a coil, as desired. Various designs can be used. Stimulus delivery in the illustrative system may use any chosen pair or combination of three or more electrodes; in one example, stimulus is provided between electrodes 108 and 112. The canister 102 is shown as having an isolated button electrode 112; in other embodiments much of the exterior of the canister, rather than an isolated portion, can be used as an electrode. A programmer 114 is also shown, and may be used as is known in the art to communicate with the implanted system to perform various diagnostic, programming, testing and other functions. A single vector may be selected for sensing, or multiple vectors may be used simultaneously.

The system of FIG. 4 is shown as a subcutaneous-only system lacking transvenous, endocardial and/or epicardial electrodes. The location is illustrated with a parasternal lead 104 extending from a lateral canister approximately located at the left axilla of the patient, such that electrode 110 is near the xiphoid of the patient with electrodes 108 and 106 more superiorly located along the sternum. Other subcutaneous-only implant locations can also be used, including anterior-posterior placements, anterior only placement, and/or lateral-posterior placement.

Figure 5:
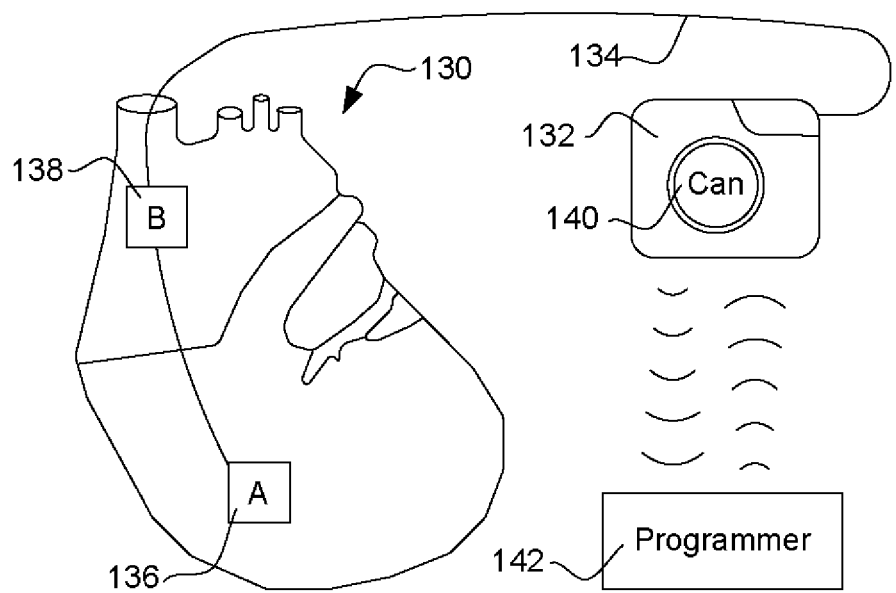
FIG. 5 shows an illustrative transvenous implantable defibrillator.

FIG. 5 shows an illustrative transvenous implantable defibrillator. The transvenous system is shown relative to the patient's heart 130 and includes a canister 132 coupled to a lead 134 that extends transvenously into the heart 130 through the using venous access via the subclavian vein. The lead 134 includes electrodes 136, 138 that are disposed within the heart, and the canister 132 includes a canister electrode 140. A programmer 142 is again provided for communication with the implanted system.

The implanted systems can use any suitable technology for such aspects as the lead design, electrodes, canister design, electronics, batteries, communication circuitry etc. In one illustrative example, the canister contains operational circuitry including input circuitry having passive filtering components, a vector selection switch array, one or more ECG amplifiers and analog-to-digital conversion circuitry. A microcontroller may receive signal from this input circuitry. Various battery chemistries can be used, such as lithium-magnesium battery cells. Illustrative output circuitry that can also be part of the operational circuitry may include an H-bridge-type system having multiple legs and high and low sides with high power switches that enable multi-phasic therapy delivery. Therapy may be delivered from capacitors that can be charged with a charging circuit (such as a flyback transformer circuit) taking current from the battery cells, each of which may also be part of the operational circuitry. The canister itself may be formed of titanium, stainless steel or other suitable material and may include coatings such as titanium nitride, iridium oxide, porous carbon, etc. The leads may be formed of suitable biocompatible materials such as silicone, polyurethane, polycarbonate, and/or blends thereof or other polymers, coated or uncoated. The leads may contain conductors made, for example, with stainless steel (including MP35N alloy), silver, etc., in various forms including drawn filled tube designs. The electrodes can be coated or uncoated and may also be formed of suitable materials such as MP35N and other stainless steels, platinum, gold, silver, or titanium, for example.

Figure 6:
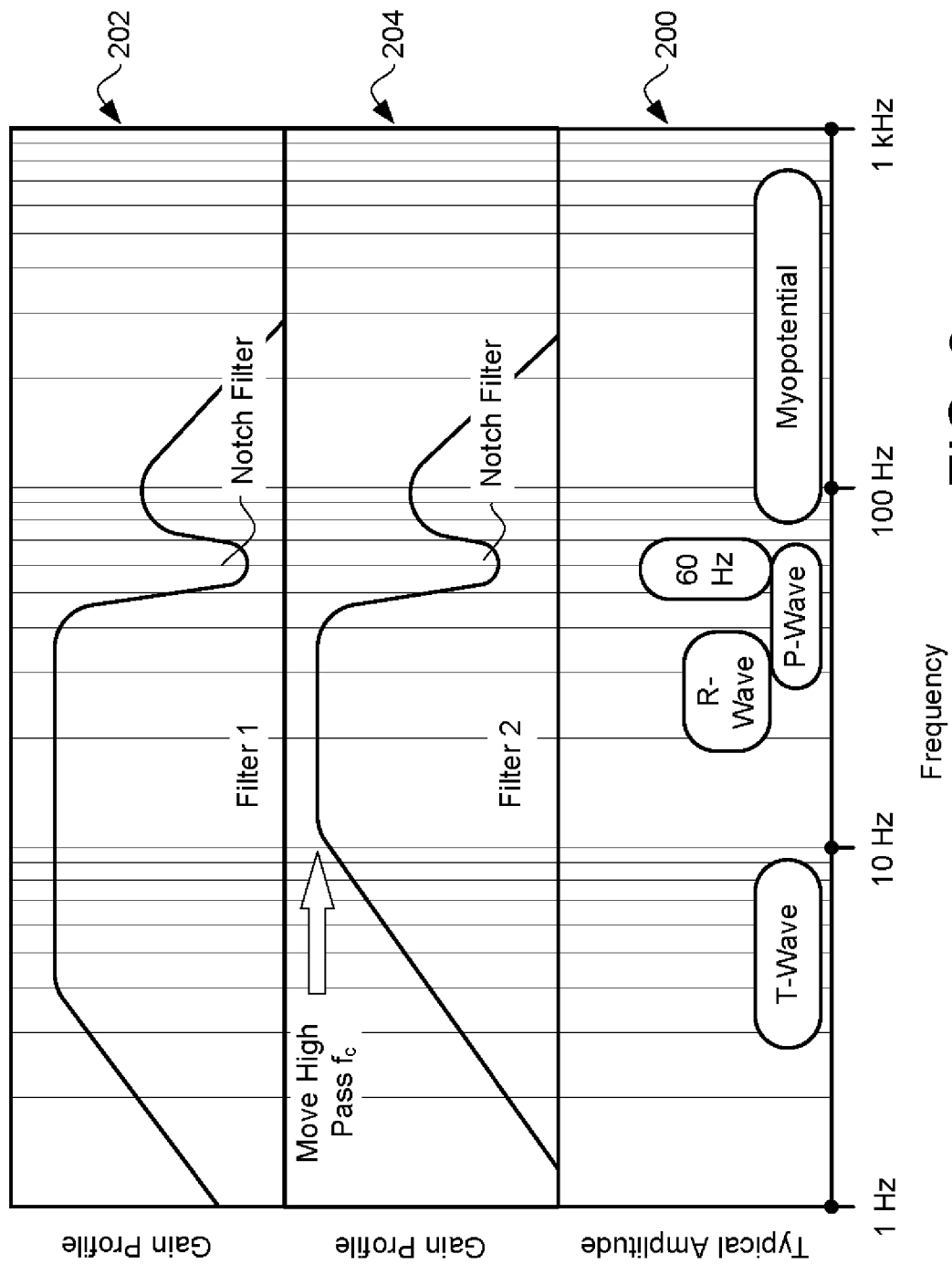
FIG. 6 shows frequency content and filter response for an illustrative embodiment.

FIG. 6 shows frequency content and filter response for an illustrative embodiment. Although presented in a form similar to a Bode plot, the graphic in FIG. 6 is merely illustrative and is not necessarily to scale.

The chart of typical amplitudes versus frequency, as shown in FIG. 1, is condensed for illustration as shown at 200. Two filter gain profiles are shown at 202 and 204. Filter 1, shown at 202, has a gain profile that allows maximum gain across frequencies from about 4 Hz to about 50 Hz, with a notch at 60 Hz and attenuation at higher frequencies. Filter 2, shown at 204, as a gain profile that allows maximum gain across a smaller range of frequencies, attenuating the T-waves occurring below 10 Hz to a greater extent than Filter 1. As indicated, the High Pass corner frequency is moved out to about 10 Hz. While a relatively gradual slope is shown, those skilled in the art will recognize that digital filter designs in particular can provide steep gain dropoff at desired corner frequencies.

In some examples, rather than Notch filter at the line frequency, the system may use a low pass filter having a very steep profile in the range of 40 Hz or so, which will function to attenuate line frequencies in various geographies.

The following US Patents, application publications, and provisional applications are incorporated herein by reference as illustrative examples for design, operation and implantation of cardiac devices: U.S. Pat. No. 6,647,292, titled UNITARY SUBCUTANEOUS ONLY IMPLANTABLE CARDIOVERTER-DEFIBRILLATOR AND OPTIONAL PACER; U.S. Pat. No. 6,721,597, titled SUBCUTANEOUS ONLY IMPLANTABLE CARDIOVERTER-DEFIBRILLATOR AND OPTIONAL PACER; U.S. Pat. No. 6,754,528, titled APPARATUS AND METHOD OF ARRHYTHMIA DETECTION IN A SUBCUTANEOUS IMPLANTABLE CARDIOVERTER/DEFIBRILLATOR; U.S. Pat. No. 7,149,575, titled SUBCUTANEOUS CARDIAC STIMULATOR DEVICE HAVING AN ANTERIORLY POSITIONED ELECTRODE; U.S. Pat. No. 7,330,757, titled METHOD FOR DISCRIMINATING BETWEEN VENTRICULAR AND SUPRAVENTRICULAR ARRHYTHMIAS; U.S. Pat. No. 7,248,921, titled METHOD AND DEVICES FOR PERFORMING CARDIAC WAVEFORM APPRAISAL; U.S. Pat. No. 7,392,085, titled MULTIPLE ELECTRODE VECTORS FOR IMPLANTABLE CARDIAC TREATMENT DEVICES; US Patent Application Publication Number 2006-0122676, titled APPARATUS AND METHOD FOR SUBCUTANEOUS ELECTRODE INSERTION, now U.S. Pat. No. 7,655,014; U.S. Pat. No. 7,376,458, titled METHOD FOR DEFINING SIGNAL TEMPLATES IN IMPLANTABLE CARDIAC DEVICES; U.S. Pat. No. 7,477,935, titled METHOD AND APPARATUS FOR BEAT ALIGNMENT AND COMPARISON; US Patent Application Publication Number 2006-0167503, titled METHOD FOR ADAPTING CHARGE INITIATION FOR AN IMPLANTABLE CARDIOVERTER-DEFIBRILLATOR, now U.S. Pat. No. 8,160,697; US Patent Application Publication Number 2009-0228057, titled ACCURATE CARDIAC EVENT DETECTION IN AN IMPLANTABLE CARDIAC STIMULUS DEVICE; US Patent Application Publication Number 2009-0259271, titled METHODS AND DEVICES FOR ACCURATELY CLASSIFYING CARDIAC ACTIVITY, now U.S. Pat. No. 8,160,686; U.S. Pat. No. 7,623,913, titled IMPLANTABLE MEDICAL DEVICES USING HEURISTIC FILTERING IN CARDIAC EVENT DETECTION; U.S. Pat. No. 7,623,909, titled IMPLANTABLE MEDICAL DEVICES AND PROGRAMMERS ADAPTED FOR SENSING VECTOR SELECTION; US Patent Application Publication Number 2009-0036944, titled ELECTROMAGNETIC INTERFERENCE SHIELDING IN AN IMPLANTABLE MEDICAL DEVICE, now U.S. Pat. No. 7,769,457; US Patent Application Publication Number 2009-0198296, titled ADAPTIVE SHOCK DELIVERY IN AN IMPLANTABLE CARDIAC STIMULUS DEVICE, now U.S. Pat. No. 8,244,349; US Patent Application Publication Number 2009-0187227, titled DATA MANIPULATION FOLLOWING DELIVERY OF A CARDIAC STIMULUS IN AN IMPLANTABLE CARDIAC STIMULUS DEVICE; U.S. Provisional Patent Application Ser. No. 61/221,316, titled CONFIRMATION OF TREATABLE ARRHYTHMIA IN IMPLANTABLE CARDIAC STIMULUS DEVICES; U.S. Provisional Patent Application Ser. No. 61/255,249, titled METHODS AND DEVICES FOR IDENTIFYING OVERDETECTION OF CARDIAC SIGNALS; and U.S. Provisional Patent Application Ser. No. 61/255,253, titled ADAPTIVE WAVEFORM APPRAISAL IN AN IMPLANTABLE CARDIAC SYSTEM. These patents and publications are incorporated for illustrative purposes and the present invention may be used in other implantable cardiac systems as well, including monitoring systems and/or transvenous or epicardial systems.

Those skilled in the art will recognize that the present invention may be manifested in a variety of forms other than the specific embodiments described and contemplated herein. Accordingly, departures in form and detail may be made without departing from the scope and spirit of the present invention.

What is claimed is:

1. A method of cardiac signal analysis in an implantable cardiac stimulus or monitoring device, the device comprising an implantable canister housing operational circuitry and having a plurality of electrodes coupled to the operational circuitry; the method comprising:
   capturing a signal from a chosen set of the plurality of electrodes; and
   performing cardiac beat detection by comparing a detection threshold to an amplitude of the captured signal by:
   a) using a signal that undergoes post-beat filtering for a predefined period of time following the detected cardiac event; and
   b) using a signal that undergoes default filtering once the predefined period of time has expired;
   wherein the post-beat filtering is configured to attenuate frequencies correlated to T-waves more greatly than the default filtering;
   wherein the method is performed on a beat-by-beat basis, such that after detection of a cardiac beat, beat detection using the post-beat filtering is performed and, if no additional beat is detected during the predefined period of time following the detected cardiac event, beat detection using the default filtering is performed.

2. The method of claim 1 wherein the default filtering includes a default high pass filter having a corner frequency in the range of 1-5 Hz and the post-beat filtering includes a post-beat high pass filter having a corner frequency in the range of 3-10 Hz, wherein the corner frequency of the default high pass filter is lower than the corner frequency of the post-beat high pass filter.

3. The method of claim 1 wherein the default filtering includes a default high pass filter having a corner frequency in the range of about 3 Hz and the post-beat filtering includes a post-beat high pass filter having a corner frequency in the range of about 10 Hz.

4. The method of claim 1 wherein the post-beat filtering occurs for a period of time in the range of about 250 milliseconds.

5. The method of claim 1 further comprising defining a refractory period in which a new cardiac event cannot be declared following detection of a cardiac event, wherein the post-beat filtering is performed following expiration of the refractory period.

6. The method of claim 5 wherein the refractory period has a variable duration, and the sum of the duration of the refractory period and the duration of the predefined period of time for performing post-beat filtering is constant.

7. An implantable cardiac stimulus device (ICSD) comprising:
operational circuitry including a power supply, output capacitor, and microcontroller, the microcontroller controlling operations in the ICSD; and
a plurality of electrodes electrically coupled to the operational circuitry to allow sensing of cardiac events;
wherein the operational circuitry is configured to perform the following method:
capturing a signal using a selected set of the plurality of electrodes; and
performing cardiac beat detection by comparing a detection threshold to an amplitude of the captured signal by:
a) using a signal that undergoes post-beat filtering for a predefined period of time following the detected cardiac event; and
b) using a signal that undergoes default filtering once the predefined period of time has expired;
wherein the post-beat filtering is configured to attenuate frequencies correlated to T-waves more greatly than the default filtering
wherein the cardiac beat detection is performed on a beat-by-beat basis, such that after detection of a cardiac beat, beat detection using the post-beat filtering is performed and, if no additional beat is detected during the predefined period of time following the detected cardiac event, beat detection using the default filtering is performed.

8. The ICSD of claim 7 wherein the operational circuitry is further configured such that the default filtering includes a default high pass filter having a corner frequency in the range of 1-5 Hz and the post-beat filtering includes a post-beat high pass filter having a corner frequency in the range of 3-10 Hz, wherein the corner frequency of the default high pass filter is lower than the corner frequency of the post-beat high pass filter.

9. The ICSD of claim 7 wherein the operational circuitry is further configured such that the default filtering includes a default high pass filter having a corner frequency in the range of about 3 Hz and the post-beat filtering includes a post-beat high pass filter having a corner frequency in the range of about 10 Hz.

10. The ICSD of claim 7 wherein the operational circuitry is further configured such that the post-beat filtering occurs for a period of time in the range of about 250 milliseconds.

11. The ICSD of claim 7 wherein the operational circuitry is further configured such that the method also comprises defining a refractory period in which a new cardiac event cannot be declared following detection of a cardiac event, wherein the post-beat filtering is performed following expiration of the refractory period.

12. The ICSD of claim 11 wherein the operational circuitry is further configured such that the refractory period has a variable duration, and the sum of the duration of the refractory period and the duration of the predefined period of time for performing post-beat filtering is constant.

13. The ICSD of claim 7 further comprising an implantable canister housing the operational circuitry and a lead electrode assembly coupled to the implantable canister, wherein the lead electrode assembly includes at least two of the electrodes and the canister includes at least one of the electrodes.

14. An implantable medical device (IMD) comprising:
operational circuitry, the operational circuitry including a power supply, memory, and a microcontroller, the microcontroller controlling operations in the IMD; and
a plurality of electrodes electrically coupled to the operational circuitry to allow sensing of cardiac events;
wherein the operational circuitry is configured to perform the following method:
capturing a signal using a selected set of the plurality of electrodes; and
detecting cardiac events by comparing a detection threshold to an amplitude of the captured signal by:
a) using a signal that undergoes post-beat filtering for a predefined period of time following the detected cardiac event; and
b) using a signal that undergoes default filtering once the predefined period of time has expired;
wherein the post-beat filtering is configured to attenuate frequencies correlated to T-waves more greatly than the default filtering
wherein the detecting cardiac events is performed on a beat-by-beat basis, such that after detection of a cardiac beat, beat detection using the post-beat filtering is performed and, if no additional beat is detected during the predefined period of time following the detected cardiac event, beat detection using the default filtering is performed.

15. The IMD of claim 14 wherein the operational circuitry is further configured such that the default filtering includes a default high pass filter having a corner frequency in the range of 1-5 Hz and the post-beat filtering includes a post-beat high pass filter having a corner frequency in the range of 3-10 Hz, wherein the corner frequency of the default high pass filter is lower than the corner frequency of the post-beat high pass filter.

16. The IMD of claim 14 wherein the operational circuitry is further configured such that the default filtering includes a default high pass filter having a corner frequency in the range of about 3 Hz and the post-beat filtering includes a post-beat high pass filter having a corner frequency in the range of about 10 Hz.

17. The IMD of claim 14 wherein the operational circuitry is further configured such that the post-beat filtering occurs for a period of time in the range of about 250 milliseconds.

18. The IMD of claim 14 wherein the operational circuitry is further configured such that the method also comprises defining a refractory period in which a new cardiac event cannot be declared following detection of a cardiac event, wherein the post-beat filtering is performed following expiration of the refractory period.

19. The IMD of claim 18 wherein the operational circuitry is further configured such that the refractory period has a variable duration, and the sum of the duration of the refractory period and the duration of the predefined period of time for performing post-beat filtering is constant.

20. The IMD of claim 14 further comprising an implantable canister housing the operational circuitry and a lead electrode assembly coupled to the implantable canister, wherein the lead electrode assembly includes at least two of the electrodes and the canister includes at least one of the electrodes.

\* \* \* \* \*